United States Patent
Giter et al.

(10) Patent No.: US 7,468,164 B2
(45) Date of Patent: Dec. 23, 2008

(54) AUTOMATED FLUID HANDLING CARTRIDGE AND FLUID PROCESSING SYSTEM

(75) Inventors: Gershon Giter, St. Paul, MN (US); Dmitry Volovik, St. Paul, MN (US)

(73) Assignee: Expert Services Group, Inc., St. Paul, MN (US)

( * ) Notice: Subject to any disclaimer, the term of this patent is extended or adjusted under 35 U.S.C. 154(b) by 741 days.

(21) Appl. No.: 10/901,855

(22) Filed: Jul. 28, 2004

(65) Prior Publication Data
US 2006/0024211 A1 Feb. 2, 2006

(51) Int. Cl.
*B01L 3/00* (2006.01)
(52) U.S. Cl. .................................................... 422/102
(58) Field of Classification Search .................. 422/102
See application file for complete search history.

(56) References Cited

U.S. PATENT DOCUMENTS

| | | | |
|---|---|---|---|
| 3,378,963 A * | 4/1968 | Obata | 52/34 |
| 3,598,161 A * | 8/1971 | Baldwin | 141/284 |
| 3,885,438 A * | 5/1975 | Harris et al. | 73/863.81 |
| 4,981,469 A * | 1/1991 | Whitehouse et al. | 604/86 |
| 5,078,970 A | 1/1992 | Teodorescu et al. | |
| 5,558,838 A * | 9/1996 | Uffenheimer | 422/100 |
| 5,660,796 A | 8/1997 | Sheehy | |
| 6,077,713 A | 6/2000 | Dunfee et al. | |
| 6,506,611 B2 * | 1/2003 | Bienert et al. | 436/180 |
| 2001/0041152 A1 | 11/2001 | Zigler et al. | |
| 2002/0106787 A1 | 8/2002 | Benn et al. | |

FOREIGN PATENT DOCUMENTS

GB 2 057 291 A 4/1981

OTHER PUBLICATIONS

Leonard, J.; Lygo, B.; Procter, G. Advanced Practical Organic Chemistry, 2nd Edition, 1995, Chapman and Hall, Oxford England.*
International Search Report mailed Nov. 18, 2005.

* cited by examiner

*Primary Examiner*—Walter D Griffin
*Assistant Examiner*—Bobby Ramdhanie
(74) *Attorney, Agent, or Firm*—Merchant & Gould, P.C.

(57) ABSTRACT

The present invention relates to a cartridge, system, and methods that can be used for automated handling of fluids, such as blood. The cartridge can be configured to obtain a fluid sample from a sealed container, e.g., a septum sealed container. The system can be configured to handle the cartridge for operations such as obtaining a sample and/or dispensing the sample from the cartridge into, for example, a microtiter plate. The method of the invention can employ the cartridge or system of the invention.

14 Claims, 16 Drawing Sheets

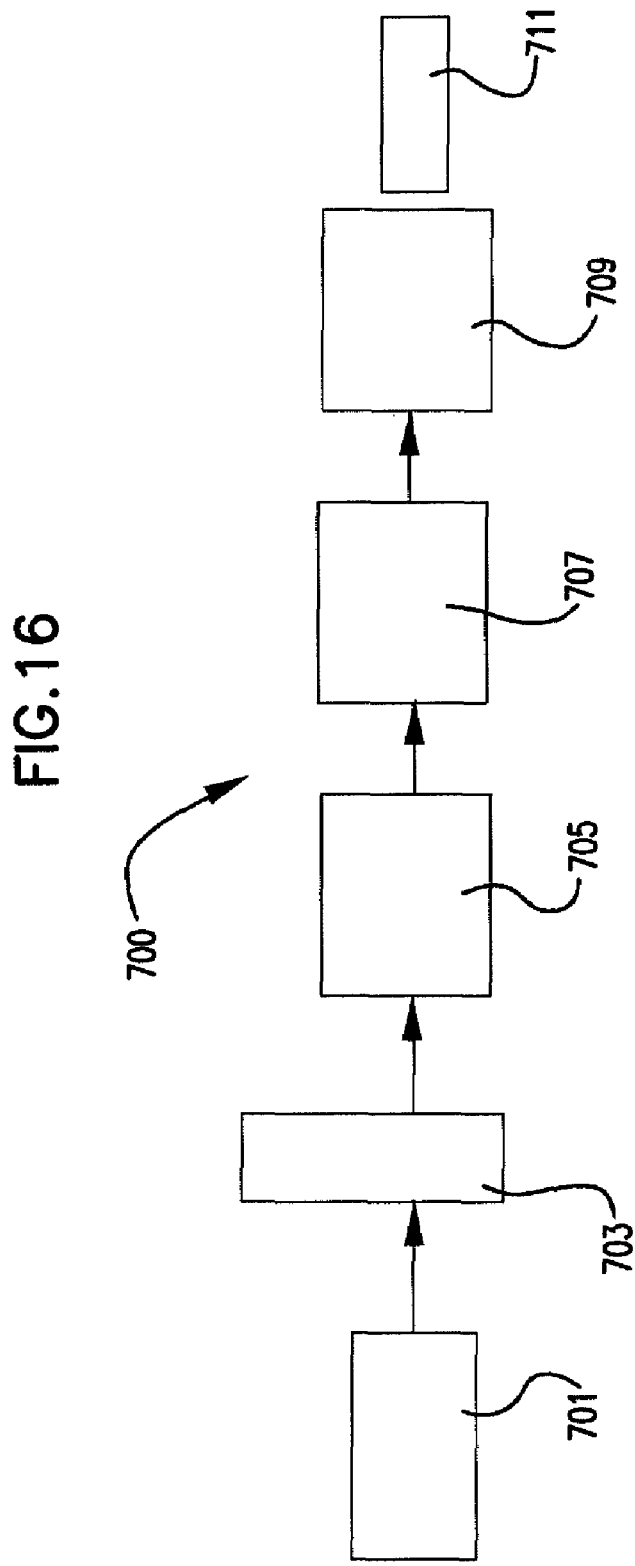

AUTOMATED FLUID HANDLING CARTRIDGE AND FLUID PROCESSING SYSTEM

FIELD OF THE INVENTION

The present invention relates to a cartridge, system, and methods that can be used for automated handling of fluids, such as blood. The cartridge can be configured to obtain a fluid sample from a sealed container, e.g., a septum sealed container. The system can be configured to handle the cartridge for operations such as obtaining a sample and/or dispensing the sample from the cartridge into, for example, a microtiter plate. The method of the invention can employ the cartridge or system of the invention.

BACKGROUND

Liquid sample processing is an everyday activity of a typical clinical, diagnostic, or research laboratory. Although the sample may include a toxic chemical or a biohazard, many conventional sample processing steps are conducted manually. Such manual processing of hazardous liquids can expose the laboratory worker to aerosols or puncture wounds. For example, sample tubes are often under either positive or negative internal pressure due to the method employed to collect the sample, changing temperature, or agitation. Opening such a tube can release an aerosol of the biohazard. Laboratories typically require employees to move samples into a large and expensive isolation hoods for opening and other steps that might release a hazardous aerosol.

Manual sample handling can compromise sample integrity. Handling dozens or hundreds of individual samples inevitably leads to human error. Human error can compromise the sample chain of custody and require costly or redundant testing and quality-control. Further, human handling of open sample tubes can lead to cross-contamination of samples.

In addition, manual sample handling can be labor intensive. Each worker can open and remove liquid from only one tube at a time. An increase in sample processing throughput is usually achieved by putting several technicians on the task in parallel. It is estimated that such manual sample processing can account for 65% of all laboratory hands-on labor costs.

In high throughput sample processing, such as whole blood or plasma analyses for infectious agents or genetic testing, large numbers of liquid samples come into the laboratories in capped and bar-coded glass or plastic vessels, e.g., VACUTAINER® tubes. Manual procedures for processing such samples can include checking the sample for clotting, scanning the barcode, verifying correspondence of sample with proper subject, placing a new number or barcode on the tube, removing the tube from a carrier, inverting the tube, uncapping the tube, disposing of the tube cap, placing the same new number or barcode on a different tube, pouring the sample into the different tube, placing the tube into a machine rack, orienting the tube for barcode reading, removing the tube from the machine rack, recapping the tube, and placing the tube into a carrier. Error in any of a variety of these labor-intensive procedures can expose a worker to hazardous substances or compromise the sample.

There remains a need for improved fluid handling systems that can rapidly and safely remove potentially harmful fluids from containers.

SUMMARY

The present invention relates to a cartridge, system, and methods that can be used for automated handling of fluids, such as blood. The cartridge can be configured to obtain a fluid sample from a sealed container, e.g., a septum sealed container. The system can be configured to handle the cartridge for operations such as obtaining a sample and/or dispensing the sample from the cartridge into, for example, a microtiter plate. The method of the invention can employ the cartridge or system of the invention.

In an embodiment, the cartridge can be in the form of a fluid receptacle. The fluid receptacle can be configured to obtain sample from sealed container. The fluid receptacle can include a piercing system, a reservoir, a vent system, and a filling system. The vent system can be configured to provide fluid communication between the container and surroundings. The vent system can be valved. The filling system can be configured to provide fluid transfer between the container and the reservoir. The filling system can include a piston. The piercing system can be configured to enter the sealed container. The piercing system can include a rigid conduit. The reservoir can be configured to contain the fluid sample.

The fluid receptacle can be a component of an apparatus also including a support. The support can be configured to retain a plurality of fluid receptacles.

In an embodiment, the present method can include a method for handling fluid samples with an automated system. The method can include removing sample fluid from a sample container into a fluid receptacle; venting the sample container with the fluid receptacle; and dispensing the sample fluid from the fluid receptacle into a second container.

BRIEF DESCRIPTION OF THE DRAWINGS

FIG. 16 schematically illustrates an embodiment of the fluid handling system according to the present invention.

DETAILED DESCRIPTION

Definitions

Figure 1:
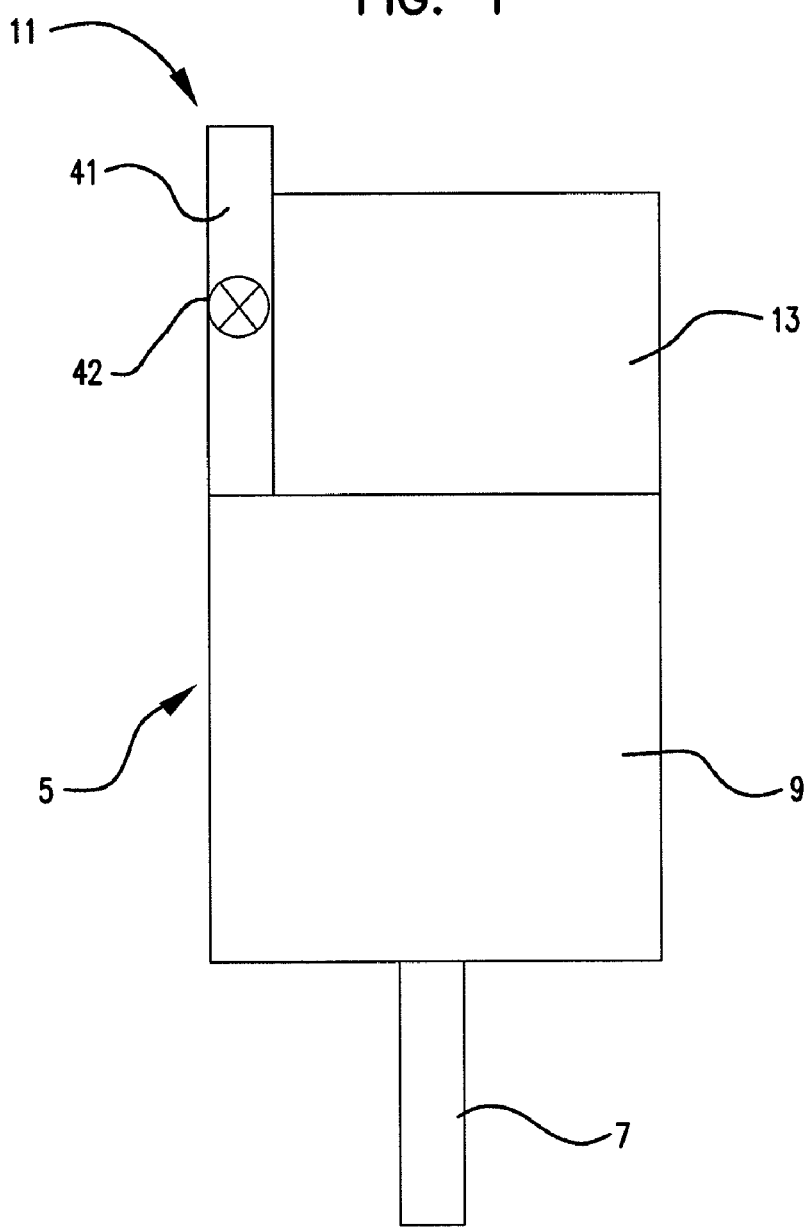
FIG. 1 schematically illustrates an embodiment of a fluid receptacle according to the present invention and including an embodiment of piercing system, reservoir, filling system, and vent system.

As used herein, the term "sealed" used in reference to a container (e.g., a tube, a vial, a jar, a bottle, or the like) refers to a container with its opening covered or obstructed by a cap, a membrane, a septum, a seal, or the like. A "capped container" is an example of a sealed container.

The Present Cartridge, System, and Methods

The present invention relates to a cartridge, system, and method that can be used for automated handling of fluids, such as blood, serum, or other biological fluids. Advantageously, in certain embodiments, the present invention can reduce the risk of exposure to biohazards, can reduce the risk of errors that may jeopardize sample integrity, and/or can reduce the amount of labor required of a laboratory technician in the course of handling fluid samples.

The cartridge can be configured to obtain a fluid sample from a sealed container, e.g., a septum sealed container. Surprisingly, in an embodiment, the cartridge can equalize pressure between the sealed container and the surroundings and obtain a fluid sample without releasing fluid (e.g., as an aerosol) from the cartridge or the container. Advantageously, in certain embodiments, the present cartridge can be configured to obtain a fluid sample from any of a variety of sizes and types of sealed containers, in a manner that need not expose a laboratory worker to aerosols, rapidly, with precision and accuracy, and/or with a reduced number of manual handling steps. Advantageously, in certain embodiments, the present cartridge can be configured to accommodate a range or variety of sample volumes, to be disposable, and/or to present a closed environment.

The system can be automated to provide high throughput sample handling and dispensing. Advantageously, in certain embodiments, the system can be programmed to provide variable sample processing speeds of up to 1000 sample containers per hour, variable acquired sample volume (e.g., about 50 to about 1000 µL), and/or variable dispensed sample volume. In an embodiment, the system can be configured to automatically read an identifying marking (e.g., a barcode) on a container without an operator being required to orient the containers in a particular fashion. Advantageously, in an embodiment, the system provides automated sample chain of custody maintenance from the sample container to the secondary container. In an embodiment, the sealed or sample container can be recovered from the system effectively sealed and ready for storage or further processing, but without an aliquot of the sample. In an embodiment, the present system can operate on containers in an order or sequence that can be predetermined or altered by the system.

The method of the invention can employ automation to remove a sample from a sealed container and dispense that sample into a secondary container. The method of the invention can include equalizing pressure between a sealed container and its surroundings and obtaining a fluid sample without releasing fluid (e.g., as an aerosol) from the cartridge or the container. The method can include high throughput sample handling and dispensing. For example, in certain embodiments, the method can include automated sampling from up to 1000 sample containers per hour, acquiring samples with any of a variety of volumes (e.g., about 50 to about 1000 µL), and/or dispensing variable sample volume. In an embodiment, the method can include machine reading of an identifying marking (e.g., a barcode) from a container without prior manual orientation of the containers. The method of the invention can employ the cartridge or system of the invention.

Cartridge

The cartridge can be configured to obtain a fluid sample from a sealed container. Surprisingly, in an embodiment, the cartridge can be configured to vent the sealed container without releasing fluid (e.g., as an aerosol) from the cartridge or the container. That is, in such an embodiment, the cartridge can include one or more filtered conduits coupling the inside of the container to its surroundings. Such a filtered conduit can provide fluid communication into a container having a negative relative pressure or out of a container having a positive relative pressure. Such fluid communication can equalize the pressure between the container and its surroundings. Such a configuration can prevent the escape of aerosols from the container of, for example, a biohazardous substance. This can provide added safety for laboratory workers.

The cartridge can be configured as a single use or disposable article that can rapidly obtain a fluid sample from a sealed container with precision and/or accuracy suitable for commercial or research purposes. The cartridge can be configured to obtain a fluid sample from any of a variety of sizes and types of sealed containers containing any of a range of volumes of fluid. Further, the cartridge can be configured to contain any of a range of sample volumes. The present cartridge can also reduce the number of manual handling steps required to obtain fluid samples from a sealed tube, especially a tube containing a toxic or hazardous substance.

For removing a sample from a sealed container, a portion of the cartridge can be configured to enter the sealed container without removing the cap or seal from the container. For example, the cartridge can be configured to insert one or more conduits through the seal on the container. Advantageously, the cartridge can be configured to vent or to equalize pressure between the surroundings and the interior of the sealed container. In an embodiment, the cartridge can be configured to filter any fluid or aerosol vented from the container through the cartridge before it enters the surroundings. In an embodiment, the cartridge can be configured to trap any liquid vented from the container through the cartridge before it enters the surroundings.

The cartridge can be configured to withdraw a fluid sample from the container. The cartridge can be configured to insert one or more conduits into the container. The cartridge can be configured to draw the fluid through the conduit and into a chamber. The cartridge can be configured to retain the fluid in the chamber. In an embodiment, the cartridge can be configured to dispense the retained fluid without processing or otherwise altering that fluid.

In an embodiment, a plurality of cartridges can be configured together. For example, a plurality of cartridges can be configured in a rack with spacing so that each of the plurality of cartridges can be positioned in proximity with each of a plurality of sealed containers for obtaining a sample. By way of further example, a plurality of sealed sample containers can be positioned in proximity to a plurality of cartridges to facilitate transfer of the samples to the cartridges. The rack of cartridges can be configured for mating with a rack of sealed containers. In an embodiment, the rack of cartridges and the rack of sealed containers can be coupled to form an integral unit.

In an embodiment, the cartridge and the rack can be configured to position the cartridge at any of several positions relative to the rack. For example, the portion of the cartridge that enters the sealed container can be positioned within the rack. Alternatively, the portion of the cartridge that enters the sealed container can protrude from the rack a sufficient distance that it can enter the container. In an embodiment, the cartridges can be removed from the rack. A rack of sealed containers can include containers positioned proximal to or distal from the portion of the rack that can mate with a rack of cartridges.

Embodiments of the Cartridge and its Support

In an embodiment the cartridge can be a component of an apparatus. The apparatus can include the cartridge in the form of a fluid receptacle. The fluid receptacle can be configured to obtain a sample (e.g., a fluid sample) from a sealed container. The fluid receptacle can include at least one of a piercing system, a reservoir, a vent system, and a filling system. In such an embodiment, the vent system can be configured to provide fluid communication between the sealed container and surroundings. The filling system can be configured to provide fluid transfer between the sealed container and the reservoir. The piercing system can be configured to enter the sealed container. The reservoir can be configured to contain the fluid sample. The apparatus can include a plurality of fluid receptacles.

The apparatus can also include a support. The support can be configured to retain a plurality of fluid receptacles. In an embodiment, the support can include a support body and a plurality of receptacle retainers. One or more of the receptacle retainers can be occupied by a fluid receptacle. In an embodiment, a plurality of fluid receptacles themselves form the support. In an embodiment, the support can be configured to couple to a rack. The rack can be configured to contain a plurality of sealed containers.

In an embodiment, the fluid receptacle can include alignment fins configured for reversibly engaging the support. In such an embodiment, the support can define one or more alignment grooves, which can be configured to engage the alignment fins. In an embodiment, the fluid receptacle can include one or more positioning projections, which can be configured for reversibly engaging the support. In such an embodiment, the support can define fluid receptacle channel and positioning grooves. The fluid receptacle channel can be configured to house a fluid receptacle. The positioning grooves can be configured to reversibly engage the positioning projections.

In an embodiment, the fluid receptacle can include the piercing system, the reservoir, the filling system, and the vent system. In an embodiment, the piercing system can include a rigid conduit. The rigid conduit can be configured to provide fluid communication from the container to the reservoir. In an embodiment, the rigid conduit can include or be a needle. In an embodiment, the reservoir includes reservoir housing. The reservoir housing can define a fluid chamber. In an embodiment, the filling system can include a first piston. The first piston can be configured for reciprocal motion. The first piston can sealably engage the reservoir housing. Reciprocal motion of the first piston can draw fluid into the fluid chamber through the rigid conduit. The reverse reciprocal motion of the first piston can expel fluid from the fluid chamber. In an embodiment, the first piston can include the first seal.

In an embodiment, the fluid receptacle can include the piercing system, the reservoir, the filling system, and a valved vent system. In an embodiment, the valved vent system can include second piston, filter, first vent conduit, second vent conduit, and vent body. The first piston can define first vent conduit and second vent conduit. The first vent conduit, the vent body, and the second vent conduit can be configured to provide fluid communication from the rigid conduit to the surroundings of the fluid receptacle. The filter can be configured to filter fluid passing from first vent conduit to second vent conduit.

In such an embodiment, the second piston can be configured for reciprocal motion and to sealably engage the valve body. The second piston can be configured to reciprocate from a position removed from the second conduit to a position obstructing flow of fluid from the first vent conduit to the second vent conduit. In an embodiment, the second piston can include a second seal.

In an embodiment, the vent system can include rigid conduit, fluid channel, and filter. In this embodiment, the rigid conduit and the fluid channel can be configured to provide fluid communication between the container and the filter. The filter can be configured to retain liquid and solid. The filter can be configured to provide communication of gasses from the fluid channel to the surroundings. In an embodiment, the rigid conduit can include or be a needle.

An embodiment with one or more needles can also include one or more sheaths. A single sheath can enclose portions of one or more (e.g., two) needles. In an embodiment including a needle and a sheath, the sheath can be configured to enclose at least a portion of the needle.

In an embodiment, the cartridge can be configured to contain a sample of a volume as small as, for example, about 50 μL to as much as about 1,000 μL. In an embodiment, the cartridge can be produced by automated assembly. The cartridge can be any of a variety of cross-sectional shapes, for example, round, oblique, rectangular, or square.

The cartridge can be configured to couple to or enter any of a variety of types and configurations of sealed containers. The sealed container can be sealed with any of a variety of seals, caps, or septa. For example, in certain embodiments, the cartridge can be configured to enter a container sealed with a VACUTAINER® or HEMOGARD® type tube cap. The sealed container can be any of a variety of sample tubes having any of a variety of lengths and diameters. In certain embodiments, the cartridge can be configured to couple to and/or remove a sample from the tube with a height of about 75 mm to about 125 mm and a diameter of about 9 to about 16 mm. For example, the tube length can be 47, 64, 75, 82, 100, 120, or 125 mm. For example, the tube diameter can be 9, 10.25, 12.5, 13, 15, or 16 mm. The tubes can be made of any of the variety of materials, for example, glass or plastic. The tubes can contain any of a variety of volumes of sample, for example, about 0.5 to about 20 mL.

In an embodiment, the cartridge includes a conduit long enough to extend from a surface of the cartridge through the seal on the container and into the container. Such a cartridge can withdraw a sample from a container including any of a variety of volumes of sample provided that the container is oriented (e.g. inverted) such that the sample contacts an aperture of the rigid conduit and/or the seal of the container.

Illustrated Embodiments of the Cartridge

FIG. 1 schematically illustrates an embodiment of a cartridge according to the present invention in the form of a receptacle 5. Receptacle 5 includes embodiments of piercing system 7, reservoir 9, filling system 13, and vent system 11. The piercing system 7 can be configured to enter a sealed container. For example, the piercing system 7 can be configured to pierce a septum on the sealed container. In an embodiment, the piercing system includes at least one needle. The filling system 13 can be configured to transfer fluid from the sealed container into the reservoir 9. In an embodiment, the filling system 13 can generate a negative pressure inside the reservoir 9, which can induce fluid to enter the receptacle 5 through the piercing system 7.

The vent system 11 can be configured to provide fluid communication from the sealed container and/or the reservoir 9 to the surroundings. In an embodiment, the vent system 11 allows a positive pressure inside the sealed container and/or the reservoir 9 to be dissipated. In an embodiment, the vent system 11 allows a negative pressure inside the sealed container and/or the reservoir 9 to be relieved. In some embodiments, a filter (not shown) is disposed in fluid communication with (e.g., within) the vent system 11. Such a filter can retain liquid, solid, or aerosol that might otherwise escape from the sealed container or receptacle 5 into the surroundings.

Vent system 11 can be configured to provide selective fluid communication between the surroundings and the receptacle 5 and/or sealed container. In an embodiment, the vent system 11 can be in the form of valved vent system 41. Valved vent system 41 can include optional vent valve 42. Valved vent system 41 can be configured to provide valved fluid communication between the surroundings and the receptacle 5 and/or sealed container. For example, valved vent system 41 (e.g., vent valve 42) can be moved or altered from a first configuration that allows fluid communication between the surroundings and the receptacle 5 and/or sealed container and a second configuration that stops fluid communication between the surroundings and the receptacle 5 and/or sealed container. In an embodiment, valved vent system 41 (e.g., vent valve 42) can be in a configuration that provides fluid communication from the reservoir 9 to the surroundings with positive pressure in the reservoir 9 and that stops fluid communication from the surroundings to the reservoir 9.

Figure 2:
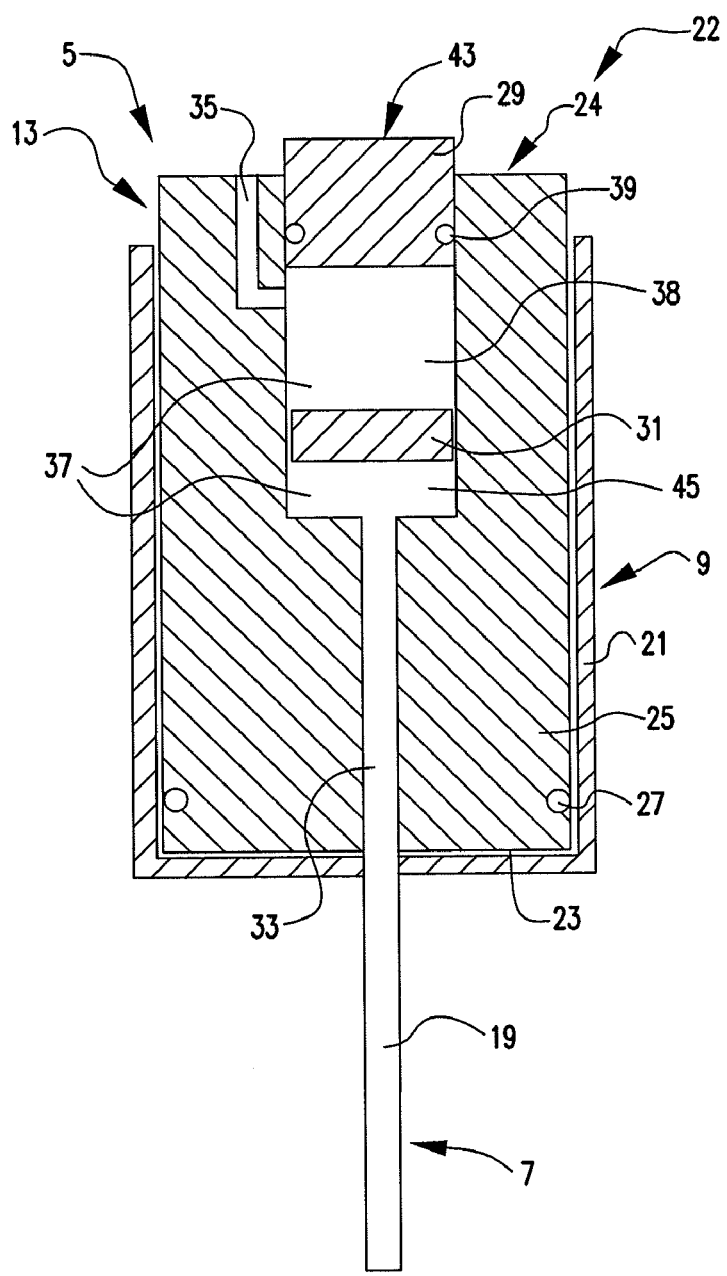
FIG. 2 schematically illustrates an embodiment of a fluid receptacle according to the present invention and including an embodiment of piercing system, reservoir, piston filling system, piston vent system, and vent filter. This Figure illustrates the fluid receptacle configured for venting a container to the surroundings.

FIG. 2 schematically illustrates another embodiment of receptacle 5 according to the present invention. FIG. 2 schematically illustrates rigid conduit 19, which is an embodiment of piercing system 7. In an embodiment, rigid conduit 19 can be in the form of a needle (not shown). Rigid conduit 19 can provide fluid communication between a sealed container (not shown) and the interior of receptacle 5. FIG. 2 schematically illustrates an embodiment of reservoir 9 in the form of reservoir housing 21, which defines fluid chamber 23 (see also, e.g., FIGS. 3 and 4).

FIG. 2 schematically illustrates piston vent system 43 as an embodiment of valved vent system 41. Piston vent system 43 includes first piston 25, second piston 29, optional filter 31, first vent conduit 33, second vent conduit 35, and second seal 39. First piston 25 defines vent chamber 37, which can house optional filter 31. In the illustrated embodiment including filter 31, first piston 25, and filter 31 define post-filter vent chamber 38 and pre-filter vent chamber 45. In this embodiment, first piston 25 defines first vent conduit 33. As shown in FIG. 2, first vent conduit 33 is configured to provide fluid communication between rigid conduit 19 and the vent chambers 45 and/or 38.

In the embodiment illustrated in FIG. 2, fluid in or entering vent chambers 38 and/or 45 can enter filter 31. Filter 31 can retain solid or liquid in the fluid, liquid, or aerosols, but allow gas to continue through vent chambers 38 and/or 45 into second vent conduit 35. Fluid (e.g., gas) can pass through second vent conduit 35 to the surroundings. Filter 31 can be positioned in the flow of fluid from first vent conduit 33 to second vent conduit 35 in a manner such that fluid must pass through the filter. For example, filter 31 can be positioned between first vent conduit 33 and second vent conduit 35 and can occupy a cross section between vent chambers 38 and 45.

In the embodiment illustrated in FIG. 2, second piston 29 is in its first position. In this first position, second piston 29 does not obstruct flow of fluid from vent chamber 38 to second vent conduit 35.

Figure 3:
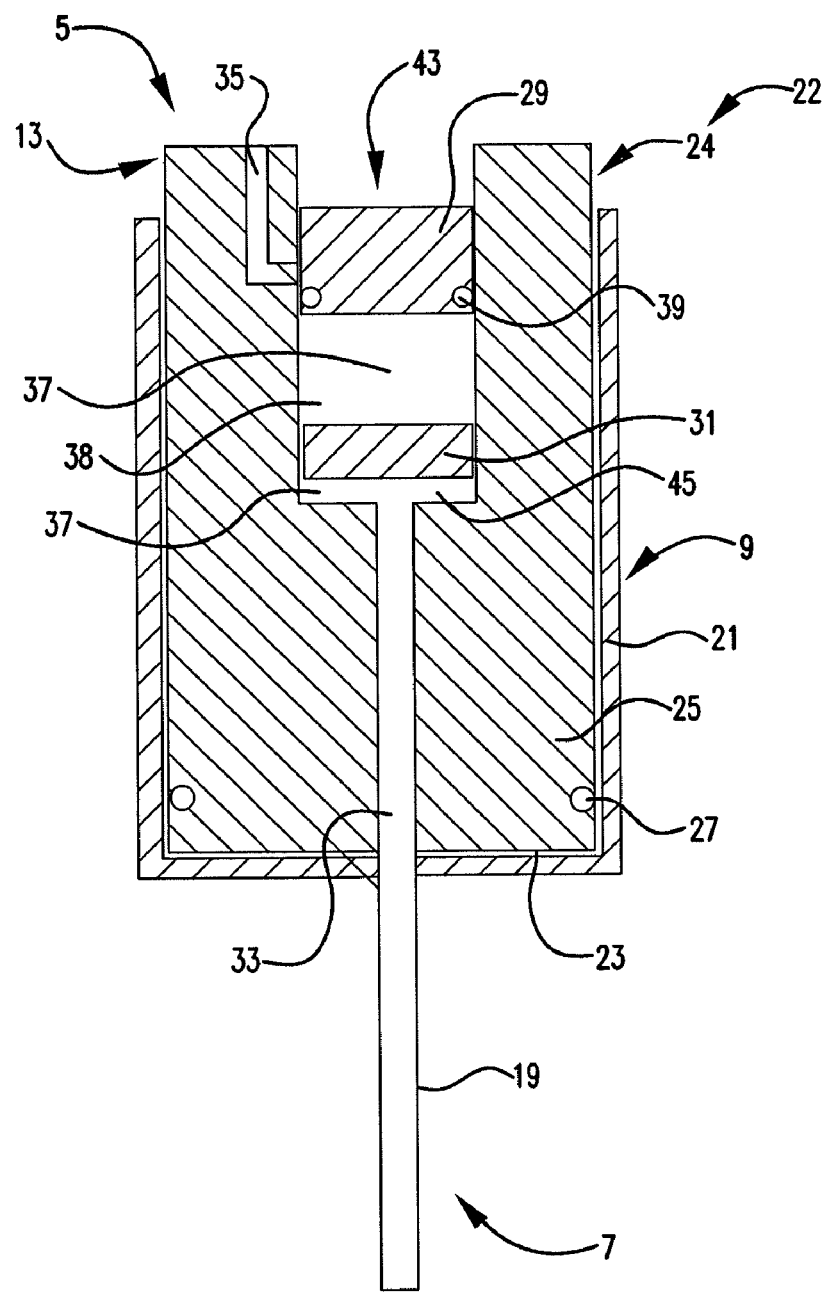
FIG. 3 schematically illustrates an embodiment of a fluid receptacle according to the present invention and including an embodiment of piercing system, reservoir, piston filling system, piston vent system, and vent filter. This Figure illustrates the fluid receptacle with the vent sealed.

As shown in FIG. 3, second piston 29 can also be deployed in its second position. In this second position, second piston 29 blocks flow of fluid from vent chambers 38 and/or 45 to or into second vent conduit 35. Piston vent system 43 can be considered closed with second piston 29 in its second position. Although FIG. 3 specifically illustrates one second position for second piston 29, it can also be deployed in any of a variety of positions that block the flow of fluid from vent chambers 38 and/or 45 to or into second vent conduit 35. Any of these variety of positions can also be considered a second position.

Second piston 29 can be moved from its first to its second position or from its second to its first position through any of a variety of mechanisms. For example, second piston 29 can be moved manually. By way of further example, second piston 29 can be moved by a fluid handling system according to the present invention. In such an embodiment, second piston 29 can include, for example, a member, cavity, or surface that can couple to or interact with an actuator portion or system of the fluid handling system.

In an embodiment, second piston 29 sealably engages first piston 25. Second piston 29 can include any of a variety of seals for this purpose. For example, second piston 29 can include an annular flap or V-seal that sealably engages first piston 25. In the illustrated embodiment, second piston 29 includes second seal 39, shown as an O-ring. Alternatively, second piston 29 and first piston 25 can be configured to provide such sealing engagement without an added seal.

FIG. 3 schematically illustrates an embodiment of filling system 13 in the form of an embodiment of a piston filling system 22, specifically a two piston filling system 24. This embodiment of a two piston filling system 24 includes first piston 25, first seal 27, second piston 29, and second seal 39. First piston 25 is disposed in fluid chamber 23 defined by reservoir housing 21. First piston 25 can be deployed in any of a variety of positions in fluid chamber 23, and, optionally, can be removed from fluid chamber 23. FIGS. 2 and 3 illustrate first piston 25 deployed in its first position with a portion (e.g., an end) proximal to rigid conduit 19.

Figure 4:
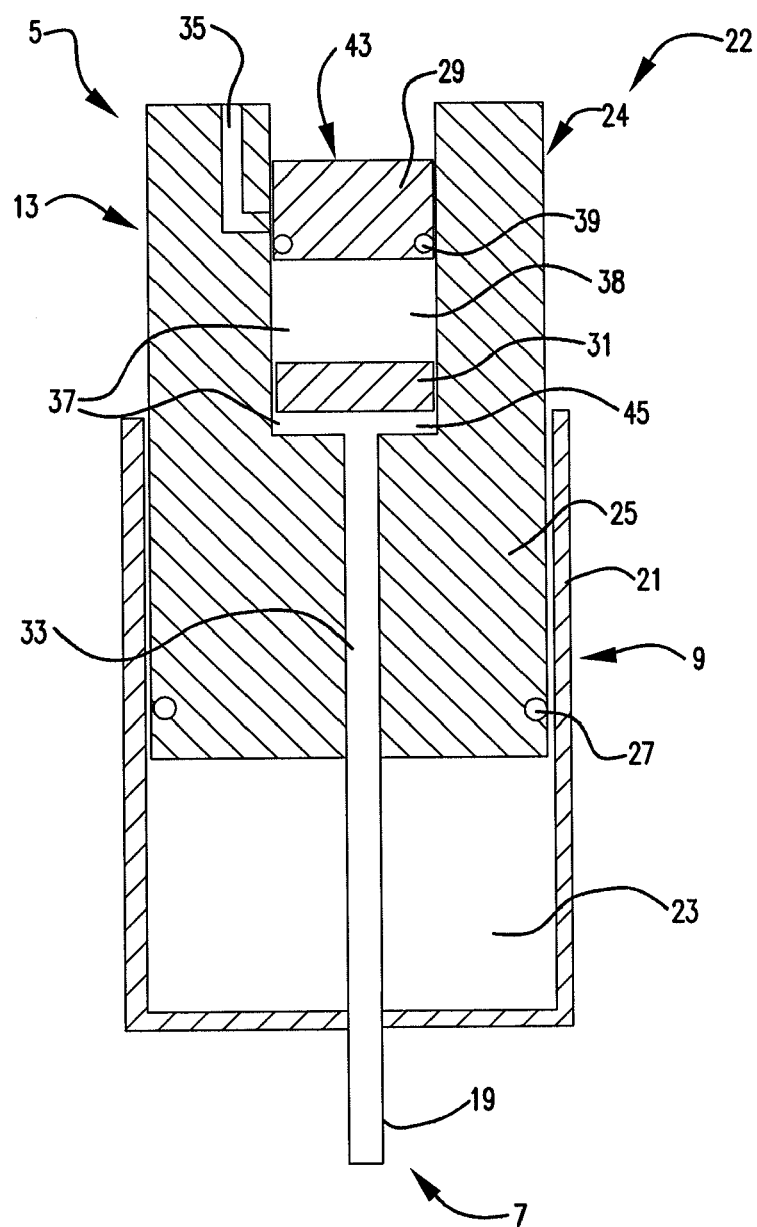
FIG. 4 schematically illustrates an embodiment of a fluid receptacle according to the present invention and including an embodiment of piercing system, reservoir, piston filling system, piston vent system, and vent filter. This Figure illustrates the fluid receptacle with the vent sealed and the filling system moved to draw or retain fluid in the reservoir.

FIG. 4 illustrates first piston 25 deployed in its second position. In its second position, first piston 25 occupies less of fluid chamber 23 than it does in its first position. With piston vent system 43 in its closed configuration, movement of first piston 25 from its first position to its second position can draw fluid through fluid conduit 19 into fluid chamber 23.

In an embodiment, first piston 25 sealably engages reservoir housing 21. First piston 25 can include any of a variety of seals for this purpose. For example, first piston 25 can include an annular flap or V-seal that sealably engages reservoir housing 21. In the illustrated embodiment, first piston 25 includes first seal 27, shown as an O-ring. Alternatively, first piston 25 and reservoir housing 21 can be configured to provide such sealing engagement without an added seal.

Operation of the embodiment of receptacle 5 illustrated in FIGS. 2, 3, and 4 can be envisioned as follows. With first piston 25 and second piston 29 each in their first positions, rigid conduit 19 can be inserted into a sealed container. In this configuration, piston vent system 43 is in its open configuration, and fluid pressure can equalize between the sealed container and the surroundings. For example, if the interior of the sealed container is at a pressure higher than the surroundings, pressure can escape the sealed container and filter 31 can retain solid or liquid (e.g., from aerosol) released with the pressure. For example, if the interior of the sealed container is at a pressure lower than the surroundings, gas from the surroundings can enter the sealed container and filter 31 can prevent liquids or solids (e.g., oil or dust) from the surroundings from entering the container. Second piston 29 can then be deployed to its second position. With second piston 29 in its second position, piston vent system is in its closed configuration. Moving first piston 25 to its second position with second piston 29 in its second position can draw fluid into fluid chamber 23 through rigid conduit 19.

Figure 5:
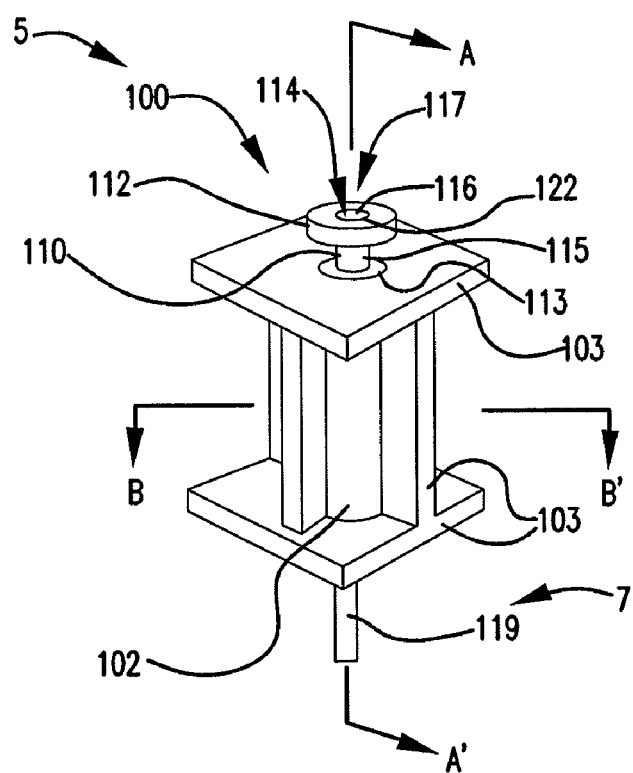
FIG. 5 schematically illustrates a perspective view of an embodiment of a fluid receptacle according to the present invention.

FIG. 5 schematically illustrates a perspective view of finned receptacle 100, which is another embodiment of receptacle 5. This embodiment also includes rigid conduit 19 as an embodiment of piercing system 7. In this embodiment, rigid conduit 19 can be in the form of a needle (not shown) and/or can provide fluid communication between a sealed container (not shown) and the interior of finned receptacle 100.

FIG. 5 schematically illustrates an embodiment of reservoir housing 21 in the form of reservoir body 102, which defines an embodiment of fluid chamber 23 (see, e.g., FIGS. 2-4). This illustrated embodiment includes fluid piston 110, which is an embodiment of first piston 25. As shown, fluid piston 110 can be positioned at least partly in reservoir body 102 and can at least partly fill fluid chamber 23. The illustrated fluid piston 110 includes flange 112 at its external end 113. Flange 112 and fluid piston 110 define groove 115. Flange 112 and/or groove 115 can couple to apparatus that can move fluid piston 110 relative to reservoir body 102. This can be accomplished, for example, by holding fluid piston 110 while moving reservoir body 102, holding reservoir body 102 while moving fluid piston 110, or moving both reservoir body 102 and fluid piston 110. In addition, flange 112 and/or groove 115 can couple to apparatus that can move finned receptacle 100.

FIG. 5 also schematically illustrates external end 117 of vent piston 116, which is disposed in a vent cavity 122 defined by fluid piston 110. Vent piston 116 defines a well 114. Well 114 can couple to apparatus that can move vent piston 116 relative to fluid piston 110 and/or reservoir body 102.

Figure 6:
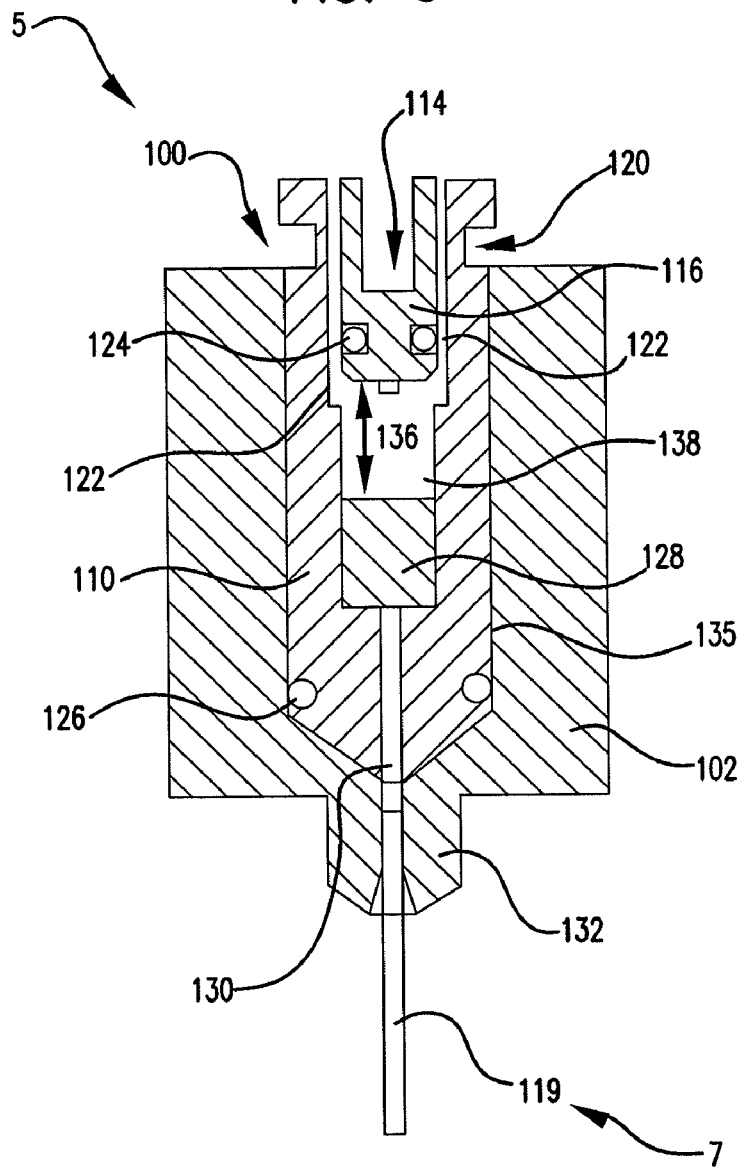
FIG. 6 schematically illustrates a cross-sectional view of the fluid receptacle of FIG. 5 cut along line A-A' and including an embodiment of piercing system, reservoir, piston filling system, piston vent system, and vent filter. This Figure illustrates the fluid receptacle configured for venting a container to the surroundings.

FIG. 6 schematically illustrates a cross-sectional view of the embodiment of receptacle 5 according to FIG. 5 taken along lines A-A'. FIG. 6 schematically illustrates an embodiment of piston vent system 43. This embodiment of piston vent system 43 includes fluid piston 110, vent piston 116, optional vent filter 128, first venting conduit 130, second venting conduit 122, and vent piston seal 124. In this embodiment, fluid piston 110 defines first venting conduit 130, at least one second venting conduit 122, and vent chamber 138. As shown in FIG. 6, first venting conduit 130 is configured to provide fluid communication between rigid conduit 119 and vent chamber 138.

The embodiment of piston vent system 43 illustrated in FIG. 6 can also include vent filter 128. Vent filter 128 is an embodiment of filter 31 and can be configured, position, and function like filter 31.

As shown in FIG. 6, vent piston 116 can be positioned at least partially in vent chamber 138. In an embodiment, vent piston 116 sealably engages second venting conduit 122 or fluid piston 110. Vent piston 116 can include any of a variety of seals for this purpose. For example, vent piston 116 can include an annular flap or V-seal that sealably engages second venting conduit 122. In the illustrated embodiment, vent piston 116 includes vent seal 124, shown as an O-ring. Alternatively, vent piston 116 and second venting conduit 122 or fluid piston 110 can be configured to provide such sealing engagement without an added seal.

Figure 9:
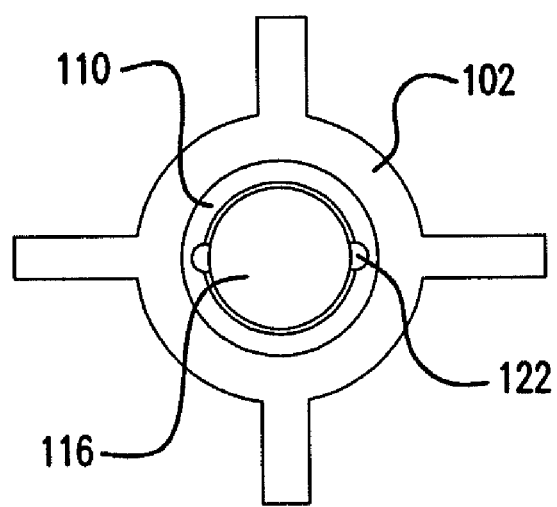
FIG. 9 schematically illustrates a cross-sectional view of the fluid receptacle of FIG. 5 cut along line B-B' and including a vent.

In the embodiment illustrated in FIG. 6, vent piston 116 is in its first position. In this first position, vent piston 116 does not obstruct flow of fluid from vent chamber 138 to second venting conduit 122. Portions of fluid piston 110 other than those forming second venting conduit 122 can contact vent piston 116 or the seal. For example, FIG. 9 illustrates an embodiment of vent piston 116 seated against fluid piston 110, except for the area of second venting conduit 122.

Figure 7:
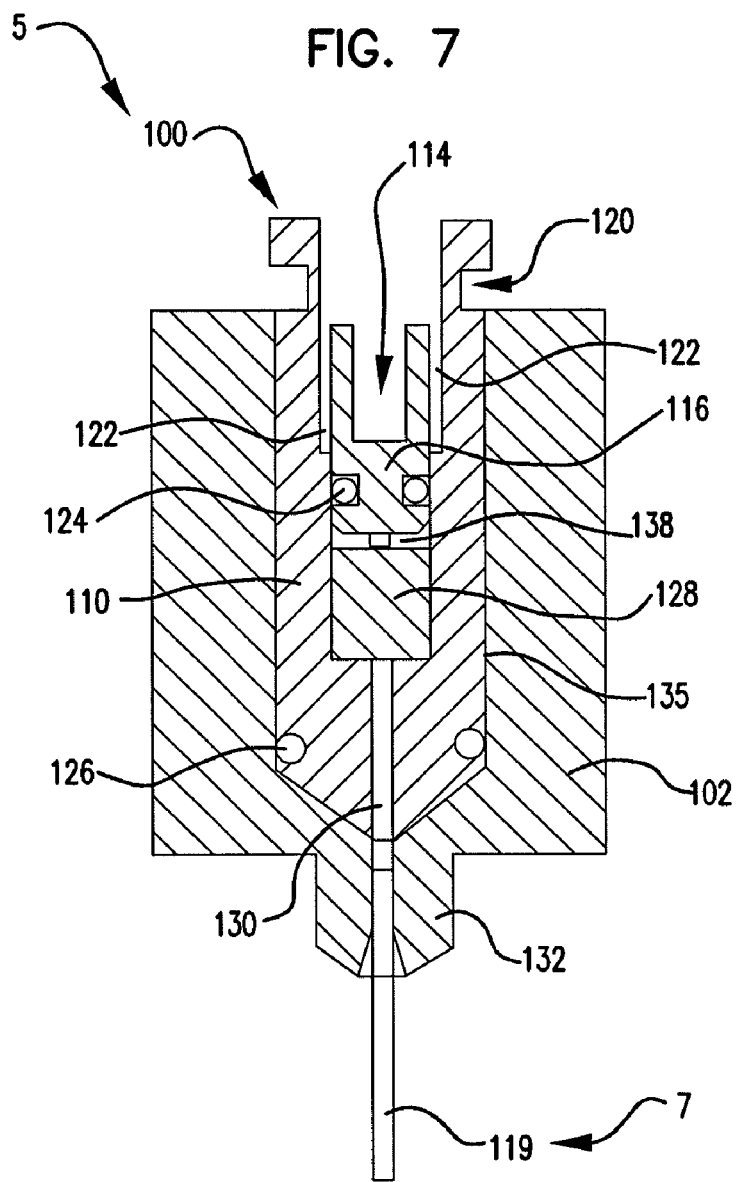
FIG. 7 schematically illustrates a cross-sectional view of the fluid receptacle of FIG. 5 cut along line A-A' and including an embodiment of piercing system, reservoir, piston filling system, piston vent system, and vent filter. This Figure illustrates the fluid receptacle with the vent sealed.

As shown in FIG. 7, vent piston 116 can also be deployed in its second position (similar to second piston 29). In this second position, vent piston 116 blocks flow of fluid from vent chamber 138 to or into second venting conduit 122. This embodiment of piston vent system 43 can be considered closed with vent piston 116 in its second position. Although FIG. 7 specifically illustrates one second position for vent piston 116, it can also be deployed in any of a variety of positions that block the flow of fluid from vent chamber 138 to or into second venting conduit 122. Any of these variety of positions can also be considered a second position.

Vent piston 116 is an embodiment of second piston 29. As such, vent piston 116 can be moved from its first to its second position or from its second to its first position through any of the variety of mechanisms suitable for moving second piston 29. For example, vent piston 116 can move reciprocally in vent chamber 138 as indicated by arrow 136 (FIG. 6).

FIG. 7 schematically illustrates an embodiment of two piston filling system 24. This embodiment of a two piston filling system 24 includes fluid piston 110, fluid piston seal 126, vent piston 116, and vent piston seal 124. Fluid piston 110 is disposed in fluid chamber 23 defined by reservoir body 102. Fluid piston 10 can be deployed in any of a variety of positions in fluid chamber 23, and, optionally, can be removed from fluid chamber 23. FIGS. 6 and 7 illustrate fluid piston 110 deployed in its first position with a portion (e.g., an end) proximal to rigid conduit 119.

As shown in FIG. 7, fluid piston 110 can be positioned at least partially in fluid chamber 23. In an embodiment, fluid piston 110 sealably engages reservoir body 102. Fluid piston 110 can include any of a variety of seals for this purpose. For example, fluid piston 110 can include an annular flap or V-seal that sealably engages reservoir body 102. In the illustrated embodiment, fluid piston 110 includes fluid piston seal 126, shown as an O-ring. Alternatively, fluid piston 110 and reservoir body 102 can be configured to provide such sealing engagement without an added seal.

Figure 8:
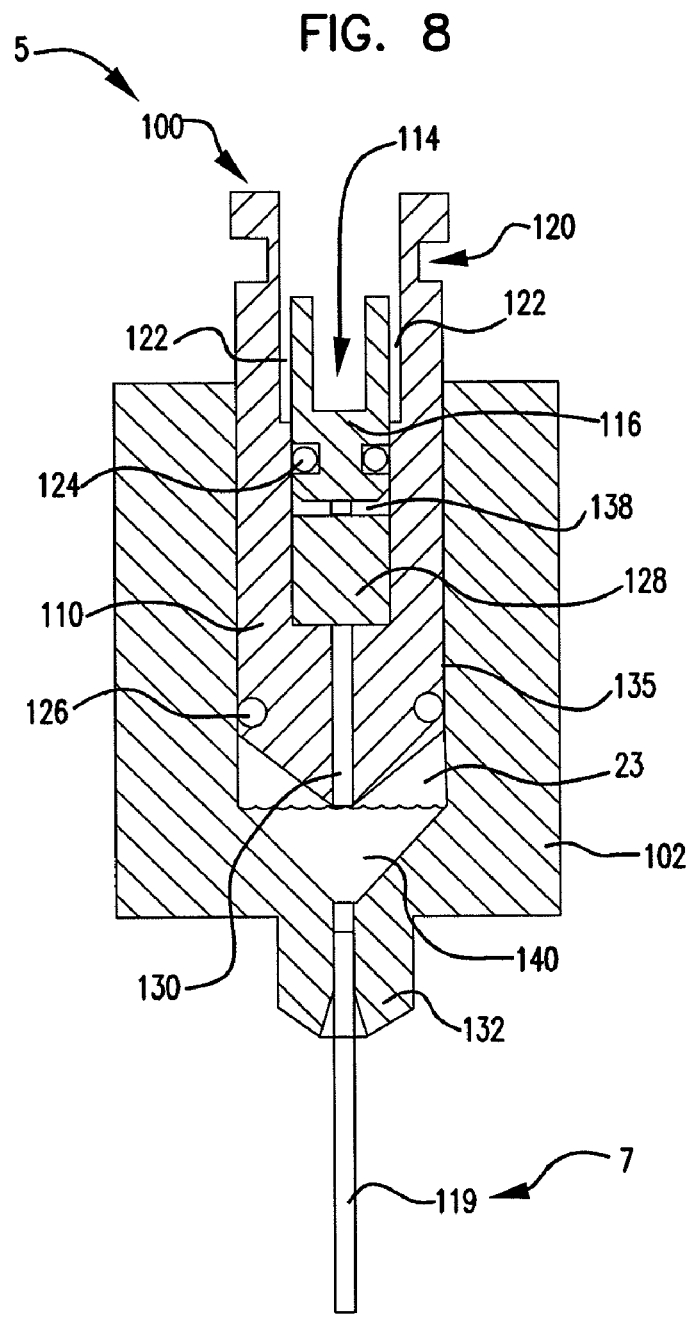
FIG. 8 schematically illustrates a cross-sectional view of the fluid receptacle of FIG. 5 cut along line A-A' and including an embodiment of piercing system, reservoir, piston filling system, piston vent system, and vent filter. This Figure illustrates the fluid receptacle with the vent sealed and the filling system moved to draw or retain fluid in the reservoir.

FIG. 8 illustrates fluid piston 110 deployed in its second position. In its second position, fluid piston 110 occupies less of fluid chamber 23 than it does in its first position. With piston vent system 43 in its closed configuration, movement of fluid piston 110 from its first position to its second position can draw fluid 140 through rigid conduit 119 into fluid chamber 23.

Operation of the embodiment of receptacle 5 illustrated in FIGS. 6, 7, and 8 can be envisioned as described above for the embodiment illustrated in FIGS. 2-4. Fluid piston 110 is an embodiment of first piston 25. Vent piston 116 is an embodiment of second piston 29.

As shown in FIG. 6, vent piston 116 is in its first position. In this first position, the vent chamber 138 is in fluid communication with the surroundings through the at least one second venting conduit 122. Vent chamber 138 can also be in fluid communication with a vent filter 128, a first venting conduit 130, and a rigid conduit 119. With vent piston 116 in its first position, fluid can pass through rigid conduit 119, first venting conduit 130, optional filter 128, vent chamber 138, and second venting conduit 122 to the surroundings. Vent piston 116 can be in its second position. With vent piston 116 in its second position, and chamber 138 is not in fluid communication with second venting conduit 122. In this second position, vent piston 116 and optional vent seal 124 occlude second venting conduit 122. With vent piston 116 in its second position, fluid cannot pass from rigid conduit 119 into the surroundings.

FIG. 9 schematically illustrates a cross-sectional view of an embodiment of reservoir body 102 and fluid piston 110 taken through cutting line B-B' of FIG. 5. This Figure shows two of second venting conduit 122, which are voids defined by fluid piston 110. This figure also shows vent piston 116 seated against fluid piston 110, except for the area of second venting conduit 122.

Illustrated Embodiments of Racks of Cartridges

Figure 10:
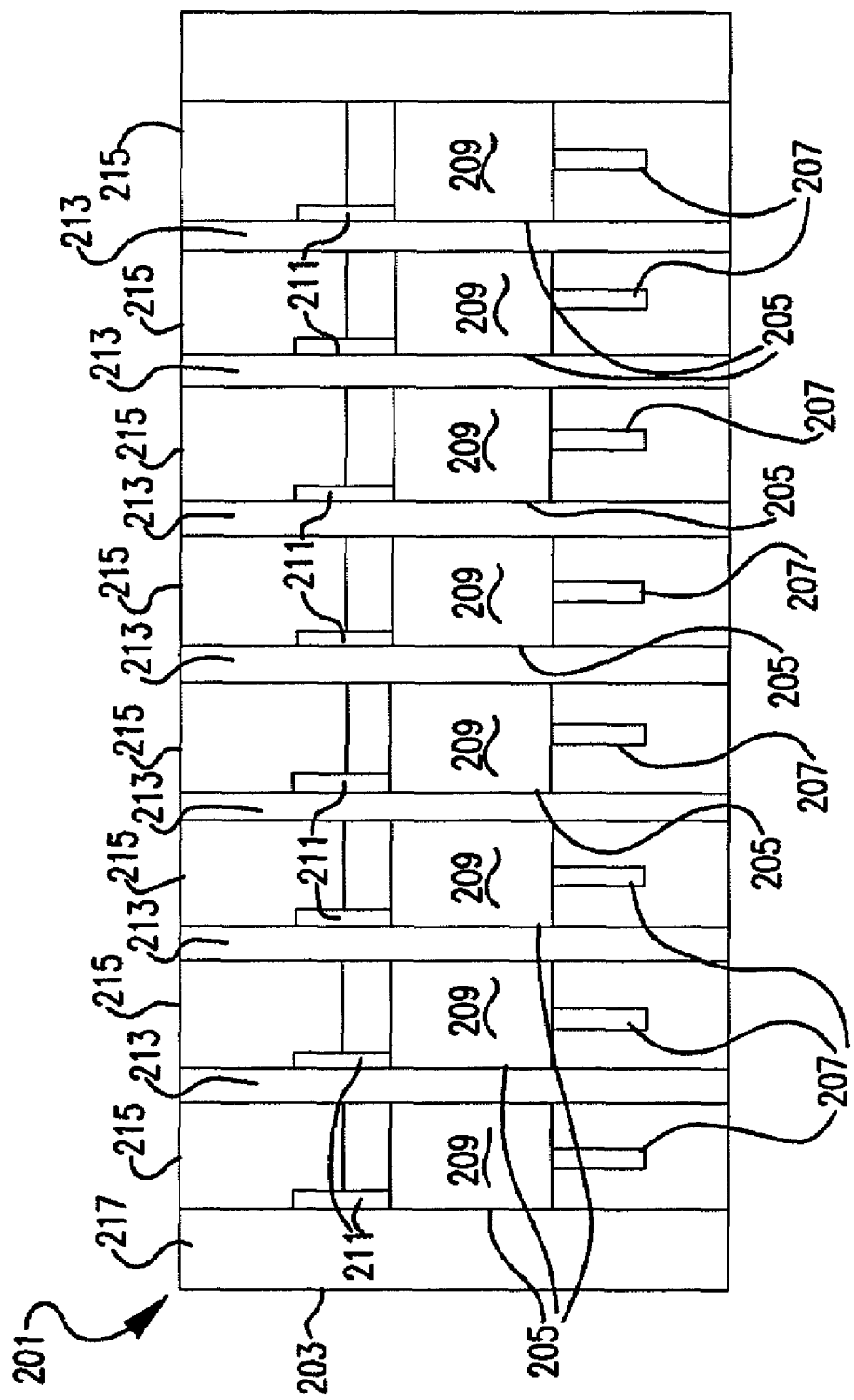
FIG. 10 schematically illustrates an embodiment of an apparatus according to the present invention and including an embodiment of support and plurality of fluid receptacles.

FIG. 10 schematically illustrates an embodiment of a rack of cartridges 201 according to the present invention. This embodiment of the rack of cartridges 201 includes a support 203 and a plurality of fluid receptacles 205. The support 203 includes a support body 217 and receptacle retainers 215 to hold on to the receptacles 205.

Figure 11:
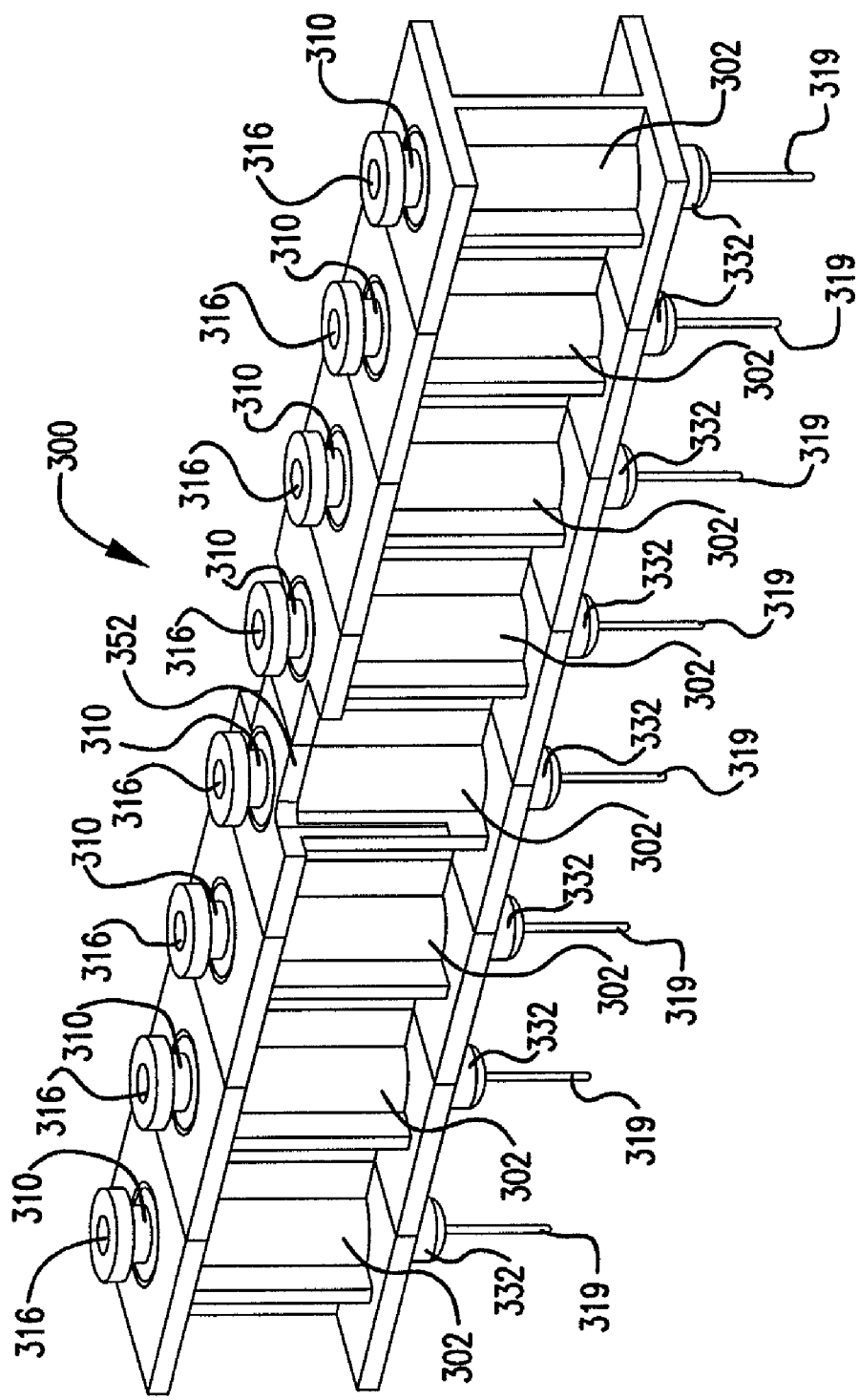
FIG. 11 schematically illustrates a plurality of fluid receptacles configured as an array in accordance with an embodiment of the invention.

FIG. 11 schematically illustrates cartridge array 300, which is another embodiment of a rack of cartridges. Cartridge array 300 includes a plurality of fluid receptacles 302 in the form of finned receptacles 100. The illustrated embodiment of cartridge array 300 is configured in the form of a strip or linear array of finned receptacles 100. In this embodiment, support 203 can be made up of portions of finned receptacles 100, for example, one or more of fins 103.

The fluid receptacles 302 in cartridge array 300 can be coupled to each other through any of a variety of mechanisms. For example, they can be coupled with a chemical adhesive or mechanically. In an embodiment, a plurality of fluid receptacles 302 can be coupled by a rack that holds the plurality of fluid receptacles 302 together as a unit. In an embodiment, one or two integral units can form a plurality of reservoir bodies 102 and fins 103. For example, the reservoir body 102 and fin 103 portions of cartridge array 300 could be molded as two halves which can be assembled with the remaining components and bonded together to form cartridge array 300.

Cartridge array 300 can define at least one optional indentation 352, which can aid in Its manipulation. Indentations 352 can be on one or both sides of the cartridge array 300. Although Figure 11 illustrates indentation 352 in the middle of cartridge rack 300, the at least One indentation 352 may be located at other positions such as toward one end of the cartridge Array 300.

Illustrated Embodiments of Racks of Cartridges and Racks of Sealed Containers

Figure 12:
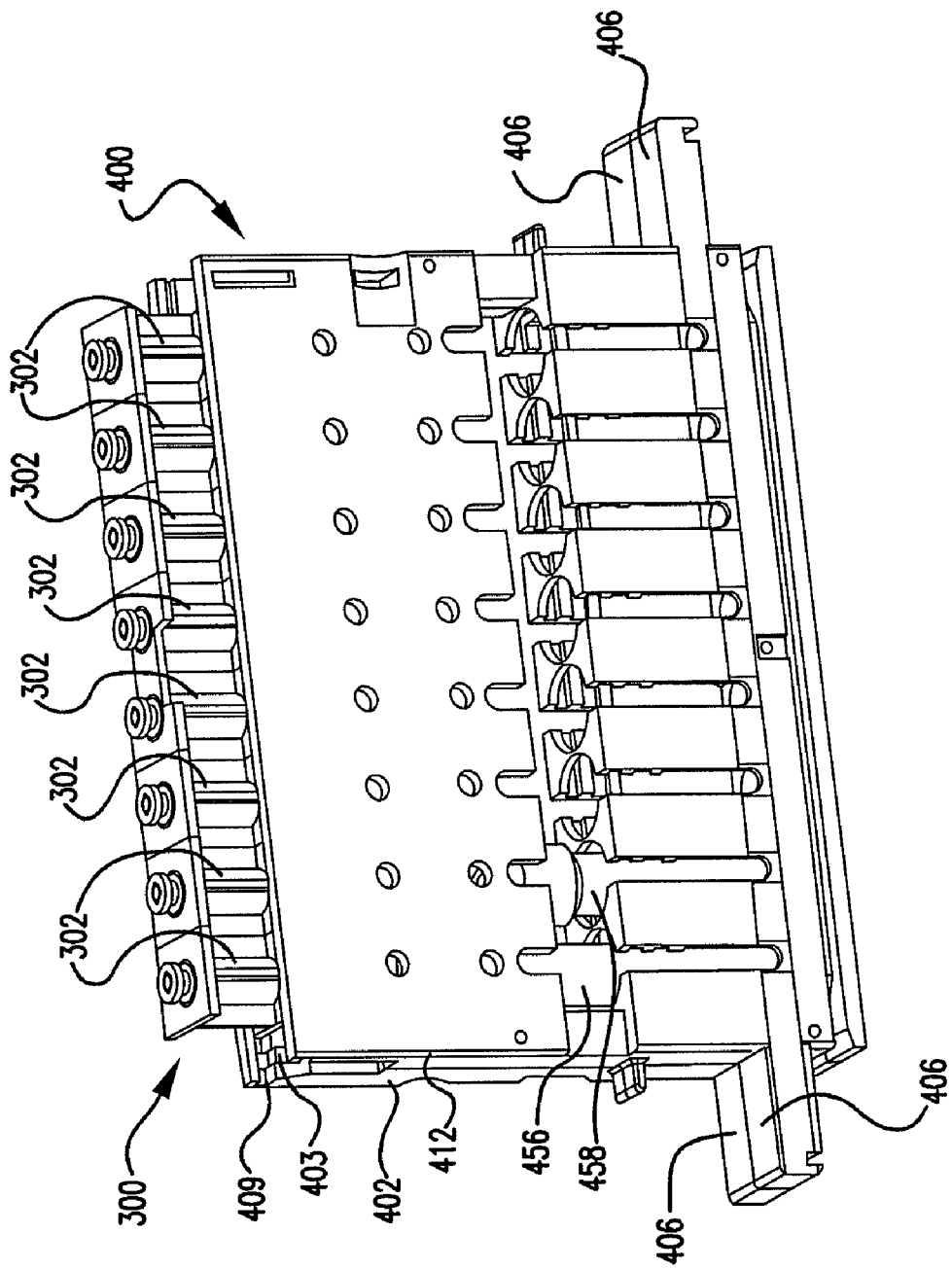
FIG. 12 schematically illustrates a sample holding rack configured with an array of fluid receptacles in accordance with an embodiment of the invention.

FIG. 12 schematically illustrates cartridge array 300 including the fluid receptacles 302 coupled to an embodiment of a rack for sealed containers, container support 400. In this view, the first side housing 402 is shown engaging a second side housing 412. The first side housing 402 and the second side housing 412 support embodiments of sealed containers, tall tube 456 and short tube 458. In this illustrated embodiment, each side housing includes at least one extension 406 and at least one guide slot 409. The guide slot 409 and extension 406 can be employed to position container support 400 and cartridge array 300 in a system that operates on these assemblies. The guide slot 409 can engage a fin 103 (shown on the bottom of the cartridge in FIG. 5) on cartridge array 300. Latch 403 can be employed to coupled one or more of cartridge array 300, first side housing 402, and second side housing 412.

Figure 13:
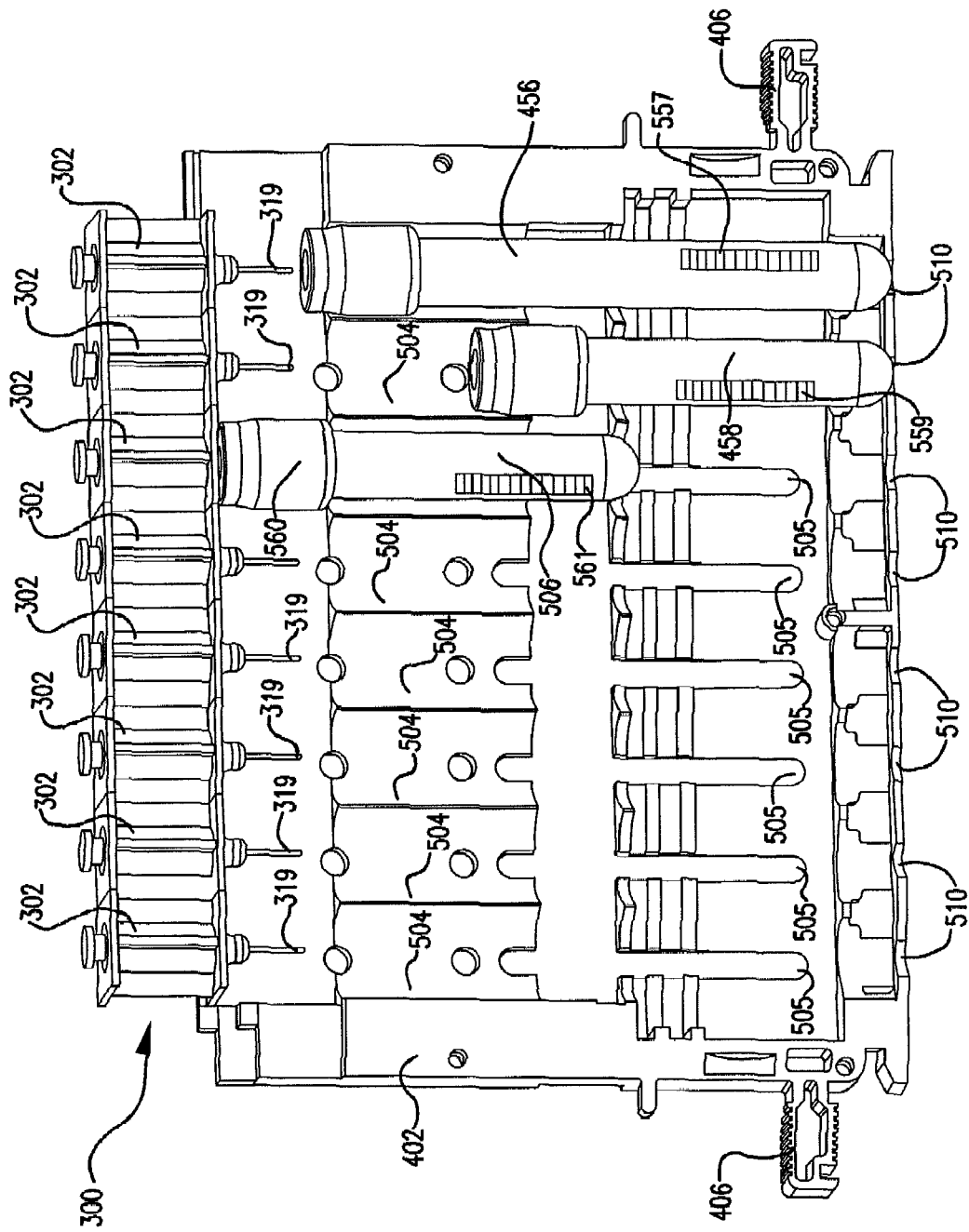
FIG. 13 schematically illustrates a sample holding rack, samples, and an array of fluid receptacles in accordance with an embodiment of the invention.

FIG. 13 schematically illustrates a partially cutaway view of the container support 400 shown in FIG. 12 coupled to cartridge array 300. This view also shows tall tube 456, short tube 458, and raised tube 506. Tall tube 456 is labeled with a first barcode 557, short tube 458 is labeled with a second barcode 559, and raised tube 506 is labeled with a third barcode 561. The tubes are illustrated with an embodiment of a sealing structure in the form of a septum cap 560. The septum cap is oriented toward rigid conduits 319 of cartridge array 300. The tubes are free to rotate around their longest axis within tube holders 504. Such rotation can allow an operator or system to rotate a tube so that its barcode can be read through code window 505, which is defined by first side housing 402.

One of skill in the art will appreciate that sample tubes of different heights can be accommodated by container support 400. FIG. 13 schematically illustrates an embodiment of container support 400 that can accommodate up to eight tubes. However, one of skill in the art will appreciate that any number of tubes can be accommodated by changing the size of the container support 400.

Figure 14:
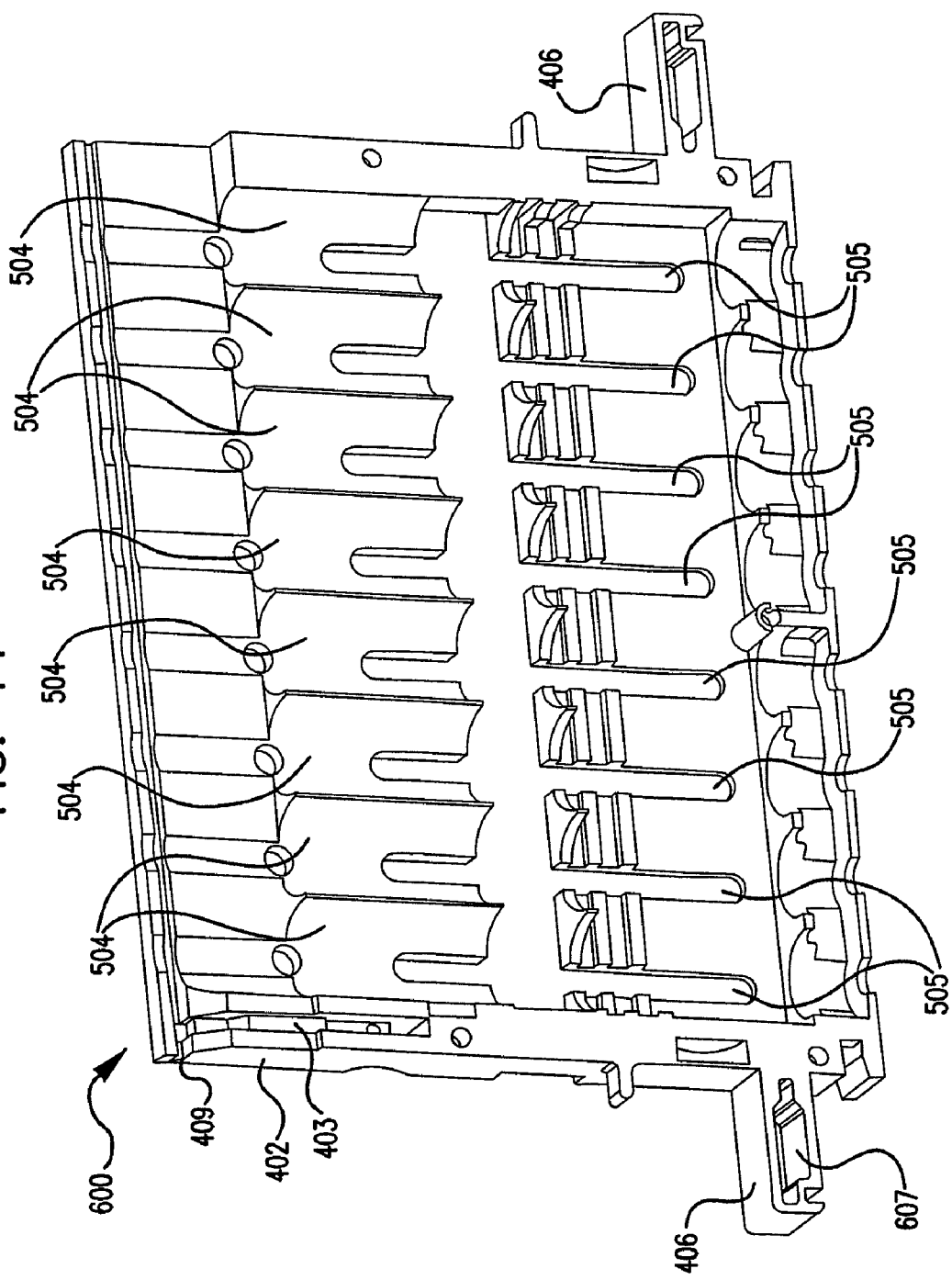
FIG. 14 schematically illustrates one half of a sample holding rack in accordance with an embodiment of the invention.

FIG. 14 schematically illustrates first side housing 402 of container support 300. First side housing 402 includes a plurality of tube holders 504 configured to retain tubes such as tall tube 456, short tube 458, and raised tube 506. First side housing 402 defines a plurality of code windows 505, through which data on the exterior of sample tubes can be read. First side housing 402 also defines fin slot 409, which can house a fin 103 of cartridge array 300 and position cartridge array 300 for coupling to a sample tube (e.g., 456, 458, or 506).

Figure 15:
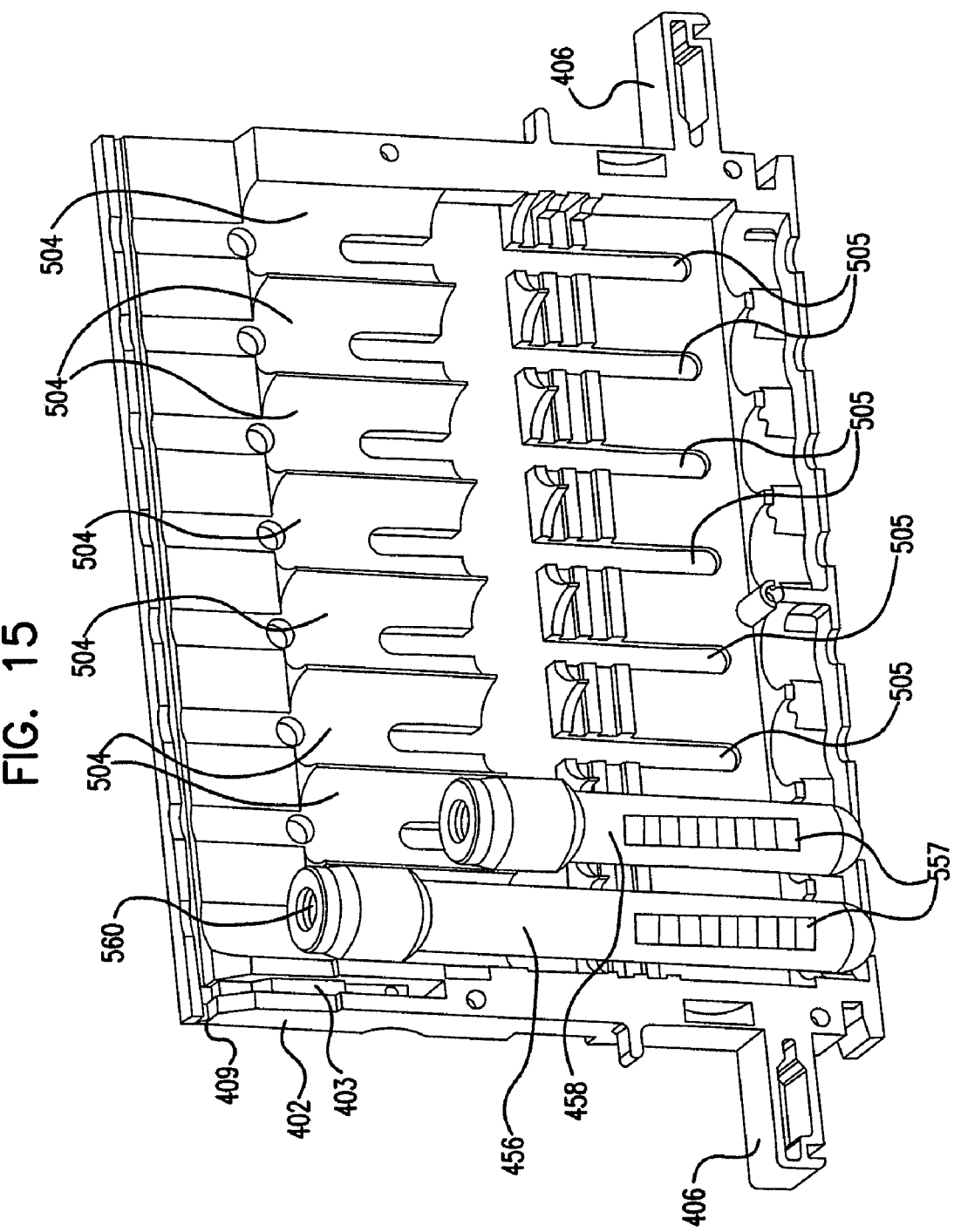
FIG. 15 schematically illustrates sample tubes disposed in one half of a sample holding rack in accordance with an embodiment of the invention.

FIG. 15 schematically illustrates first side housing 402 of container support 300 as shown in FIG. 14 and also including tall tube 456 and short tube 458 residing in tube holders 504.

Method

The present invention includes a method of handling fluids, such as blood, serum, or other biological fluids. The present method can employ the cartridge and/or system of the present invention. The present method can include equalizing pressure between a sealed container (e.g., a septum sealed container) and its surroundings, removing a sample from a sealed container (without removing the seal from the container), and/or dispensing that sample into a receptacle. In an embodiment, present method can include obtaining a fluid sample without releasing fluid (e.g., as an aerosol) from the sealed container into the surroundings.

The method can be conducted by an automated or semi-automated system. In an embodiment, the automated method can include high throughput sample handling and dispensing. Such a high throughput method can include sampling from up to 1000 sample containers per hour, acquiring samples with any of a variety of volumes (e.g., about 50 to about 1000 µL), and/or dispensing variable sample volume.

In an embodiment, the automated method can include machine reading of an identifying marking (e.g., a barcode) from a container. Advantageously, the machine reading can be conducted without prior manual orientation of the containers. For example, in an embodiment, the machine can move (e.g., rotate) the sealed container through a variety orientations including one that allows for machine reading of the identifying marking. The automated method can also include employing the identifying marking and maintaining automated sample chain of custody from the sample container to the receptacle. In an embodiment, the present method can include processing samples in a predetermined sequence. In an embodiment, the present method can include processing samples in a sequence determined by the system in response to at least one characteristic of at least one sample.

In an embodiment, the present method can include urging a conduit into a sealed container. This can be accomplished without removing the cap or seal from the container. The present method can also include venting the sealed container. Venting can include filtering any fluid entering or leaving the sealed container. Filtering can, for example, trap any solid or liquid (e.g., from an aerosol) leaving the container or any liquid or solid entering from the surroundings. The present method can also include disposing of the cartridge or other article employed for obtaining the sample after dispensing the sample.

In an embodiment, the present method can include coupling an assembly of a plurality of cartridges to an assembly of a plurality of sample containers. Such coupling can include establishing a one-to-one correspondence between the cartridges and the sample containers.

In an embodiment, the method of the invention includes venting a sealed container and trapping or filtering any fluid released from the container. The method also includes withdrawing a fluid sample from the sealed container. In an embodiment, venting and withdrawing include piercing a septum on the sealed container. Venting and withdrawing can be accomplished employing a single apparatus, such as a cartridge of the present invention. In an embodiment, the present method operates on a plurality of sealed containers at the same time. For example, the method can include positioning, at one time, a plurality of the single apparatus that accomplishes both venting and withdrawing in proximity with each of a plurality of sealed containers. The method can include operating each of the plurality of single apparatus simultaneously, at overlapping times, or in rapid sequence for venting and withdrawing.

The method can include dispensing the fluid sample. Dispensing can place the sample into any of a variety of convenient containers, such as one or more wells of a microtiter plate. In an embodiment, dispensing includes moving the apparatus (e.g., cartridge) away from the sealed container and positioning it proximal to the receiving container. In an embodiment, dispensing includes positioning, at one time, a plurality of the single apparatus that accomplishes both venting and withdrawing in proximity with each of a plurality of the receiving containers. For example, dispensing can include moving the plurality of single apparatus from a first configuration in which they are in proximity with each of a plurality of larger sealed containers to a second configuration in which one or more of the single apparatus are in proximity with one or more of a plurality smaller receiving containers (e.g., wells of a microtiter plate). Dispensing can include dispensing the contents of one or more of the single apparatus at any given time.

In an embodiment, dispensing includes withdrawing the fluid sample from the single apparatus and placing the fluid in a receiving container. For example, dispensing can include simultaneously withdrawing fluid samples from each of a plurality of single apparatus and placing the samples into each of a plurality of smaller receiving containers (e.g., wells of a microtiter plate). Dispensing can include withdrawing fluid samples from one or more of a plurality of single apparatus at any given time. In an embodiment, there are eight single apparatus and the contents of a first four single apparatus are placed into four receiving containers amongst a plurality of receiving containers, then the eight single apparatus are moved with respect to the plurality of receiving containers and the contents of a second four single apparatus are placed into four different receiving containers amongst the plurality of receiving containers. Placing the samples can include expelling the sample from the plurality of single apparatus with a piston or other source of positive pressure.

In an embodiment, the invention includes a method for handling fluid samples with an automated system including extracting sample fluid from a sample container into a fluid receptacle. The fluid receptacle can include a fluid extraction conduit and define a first cavity and include a first piston and a second piston. The first piston can be disposed in the first cavity and define a second cavity, the second piston can be disposed in the second cavity.

In an embodiment, the method can also include venting the sample container. The first piston can define a first fluid conduit and a second fluid conduit. The first fluid conduit can be in fluid communication with the fluid extraction conduit. The first fluid conduit can be in fluid communication with the first cavity. The second piston can be movable between an open position wherein the first cavity is in fluid communication with the second fluid conduit, and a closed position wherein the first cavity is not in fluid communication with the second fluid conduit. Venting the sample container can include inserting the fluid extraction conduit into the sample container with the second piston in the open position. The method can further include dispensing the sample fluid from the fluid receptacle into an output container.

Illustrated Embodiment of Method

An embodiment of the present method can be illustrated by reference to FIG. 13. FIG. 13 schematically illustrates a partially cutaway view of a container support 400 coupled to a cartridge array 300. This embodiment of the method can include placing sample tubes (e.g., 456, 458, and 506) into container support 400. The sample tubes can include an identifying barcode (e.g., 557, 559, and 561). The method can include coupling a cartridge array 300 to container support 400. Coupling can occur before or after placing. Coupling can include latching cartridge array 300 to container support 400 with a latch 403. FIG. 14 shows latch 403.

The method can include identifying each of the tubes in container support 400. Identifying can include machine reading the identifying barcode on each tube. Identifying can also include manipulating a tube to make the identifying barcode accessible for machine reading. Manipulating can include, for example, rotating the tube around its major axis. In the illustrated embodiment, manipulating can include aligning the a barcode with a code window 505, which makes the barcode visible outside container support 400.

The method can include coupling at least one tube with a cartridge. Coupling can include moving the tube in the direction of the cartridge and urging the cartridge's conduit into the tube. Alternatively, coupling can include moving the cartridge in the direction of the tube, or moving both the tube and the cartridge. Tube and cartridge are coupled when a portion of the cartridge (e.g., the conduit) is within the tube.

In the illustrated embodiment, the tube can be moved relative to the cartridge and urged onto the conduit by a shaft or other structure that can be inserted into container support 400 through aperture 510. The shaft or other structure (not shown) can move relative to the container support, or the container support can move relative to the shaft or other structure. In an embodiment, the shaft or other structure is stationary and the container support is moved relative to the shaft or other structure. For example, a shaft can move a septum sealed tube toward the cartridge and cause the conduit (illustrated as rigid conduit 319) to pierce the septum and enter the tube.

Coupling can be conducted with the vent of a vented cartridge open, allowing fluid communication between the rigid conduit in the surroundings. Such venting can be conducted as described above with reference to FIGS. 2-4 and 6-8. The method can also include removing a sample from the sample tube and/or filling the cartridge. Such removing and filling is also described above with reference to FIGS. 2-4 and 6-8.

System

The present invention includes a system that can be used for automated handling of fluids, such as blood, serum, or other biological fluids. Embodiments of the present system can operate on the present cartridge and can carry out automated embodiments of the present method. In an embodiment, the present system can operate a rack of cartridges coupled to a rack of sealed containers. Advantageously, in certain embodiments, the automated system can provide high throughput handling of racks of cartridges coupled to racks of sealed containers. For example, in an embodiment, the system can obtain samples of any of a variety of preselected volumes (e.g., about 50 to about 1000 μL) from up to about 1000 sealed containers per hour and dispense all or part of the sample into a secondary container, such as a microtiter plate. In an embodiment, the system can invert a cartridge coupled to a sealed container or a rack of cartridges coupled to a rack of sealed containers.

The system can be configured to read an identifying marking (e.g., a barcode) on a sealed container and to orient the container for machine reading, if necessary. The system can include a processor configured to associate the identifying marking with characteristics or properties of the sample, with the handling done to the sample, and/or with the destination of the sample. Such a configuration can provide automated sample chain of custody maintenance from the sample container to the secondary container. The processor can be configured to alter the order or type of processing for one or more samples in response to operator input or in response to information associated with the identified sample.

The present system can be configured to carry out one or more of a variety of procedures employed in obtaining a sample from a sealed container and dispensing it into a secondary container. For example, in an embodiment, the present system can aspirate a fluid sample from at least one sealed container, e.g., a septum sealed container, into a fluid receptacle. The present system can be configured to operate a fluid receptacle to equalize pressure between the sealed container and the surroundings. Such a system can obtain a fluid sample without releasing unacceptable fluid (e.g., as an aerosol) from the fluid receptacle and the sealed container. The system can be configured to dispense the fluid sample from the fluid receptacle into the secondary container.

Embodiments of the System

The system can be configured to handle the cartridge and/or container. In an embodiment, the system can acquire a sample from a sealed container. For example, the system can manipulate the cartridge to withdraw a sample from a sealed container. The system and cartridge can work together in a manner that obtains a sample from the sealed container without otherwise altering the sample or the container. That is, the container can be recovered effectively sealed and ready for storage or further processing, but without an aliquot of the sample.

In an embodiment, the system can dispense the sample into a secondary container, such as a microtiter plate. In an embodiment, the system can dispense a sample in portions into two or more secondary containers, e.g., wells of a microtiter plate. Advantageously, in certain embodiments, the system and the cartridge can work together to obtain and dispense samples from a plurality of containers without detectable or significant contamination of one sample with another. Advantageously, in certain embodiments, the system can rapidly obtain and dispense samples with precision and accuracy suitable for use in a commercial or research laboratory.

The fluid handling system can be configured to receive one or more sealed containers of fluid, for example, in a rack. The system can include a container receiving system. The rack of sealed containers can have been mated with a rack of cartridges by the operator, or the system can be configured to mate a rack of cartridges with the rack of sealed containers. The fluid handling system can include a cartridge receiving system and a rack mating system.

The fluid handling system can include a rack transport system. The rack transport system can be configured to transport racks of containers and/or cartridges into and through the fluid handling system. The rack transport system can operate, for example, in cooperation with or as part of the container receiving system. The rack transport system can be configured to move a rack from the container receiving system to or through subsequent subsystems of the fluid handling system.

The fluid handling system can include a sample cataloging system. The sample cataloging system can be configured to read machine-readable information (e.g., a barcode or radio frequency identification tag) on the container or rack of containers. The sample cataloging system can be configured to read machine-readable information (e.g., a barcode or radio frequency identification tag) on the secondary container. The sample cataloging system can be configured to process and store the information. The rack transport system can be configured to move a rack to, through, and/or out of the sample cataloging system.

The fluid handling system can include a sample removing system. The sample removing system can be configured to operate the cartridge to obtain a fluid sample from the sealed container. For example, in an embodiment, the sample removing system can be configured to move one or more cartridges so that a portion of the cartridge enters the sealed container. The sample removing system can be configured to operate the cartridge to draw a fluid sample from the container into the cartridge. The sample removing system can be configured to separate the cartridge from the container. In an embodiment, the sample removing system can be configured to invert the sealed container or rack of sealed containers.

The rack transport system can be configured to move a rack to, through, and/or out of the sample removing system. The rack transport system can be configured to transport a rack of sealed containers away from the sample removing system and to the exterior of fluid handling system. The rack of sealed containers can then be removed from the system and, for example, stored, disposed of, or subjected to different or additional processing steps.

The fluid handling system can include a cartridge handling system. The cartridge handling system can be configured to receive and/or operate on a cartridge that has received a fluid sample from a sealed container. The cartridge handling system can be configured to add fluid to the cartridge, to remove fluid from the cartridge, to heat the cartridge, to cool the cartridge, or to otherwise process the fluid in the cartridge. The cartridge handling system can be configured to separate the rack of cartridges from the rack of containers.

The cartridge handling system can be configured to dispense fluid from the cartridge or rack of cartridges into the second container. The cartridge handling system can be configured to dispense fluid from one or more of the cartridges in the separated rack into one or more secondary containers, e.g., wells of a microtiter plate. For example, the cartridge handling system can dispense fluid from alternate cartridges in the rack into adjacent wells of a microtiter plate. The cartridge handling system can dispense fluid from the remaining alternate cartridges in the rack into a second set of adjacent wells of a microtiter plate. The cartridge handling system can be configured to present the cartridge for disposal or to place the cartridge in a disposal container.

The system can operate on sealed containers or racks of sealed containers including any of the containers or tubes and caps or seals described above with respect to the cartridge. The system can operate on uniform or mixed sets of tube lengths and/or diameters in a single rack and/or run. In an embodiment, the present system can achieve precise and/or accurate volumes in withdrawing and/or dispensing samples through controlling the precision with which the piston is moved or the manner in which the cartridge is manipulated to withdraw and/or dispense the sample.

Illustrated Embodiments of the System

FIG. 16 schematically illustrates an embodiment of the fluid handling system according to the present invention. The illustrated embodiment includes a rack conveyor 701, an identification system 703, an aspiration system 705, optional fluid processing system 707, a fluid dispensing system 709, and/or an aliquot conveyor 711.

In this illustrated embodiment, rack conveyor 701 represents an embodiment of rack transport system. Rack conveyor 701 can be configured to receive and transport a rack of sealed containers, which can be coupled to a rack of cartridges, and transport it into and through the fluid handling system. Rack conveyor 701 can be or include any of a variety of known conveyors suitable for moving a rack of tubes.

In this illustrated embodiment, identification system 703 represents an embodiment of sample cataloging system. Identification system 703 can be configured to read indicia on the rack of cartridges, such as a barcode, a radio frequency identification tag, or the like. The indicia can provide an indication of the content of the sealed container, or processing steps for that sample. Identification system 703 can be or can include any of a variety of barcode readers, radio frequency actuators, or other known systems for reading indicia. Identification system 703 can also read indicia on a rack of containers and/or on secondary containers such as a microtiter plate.

In this illustrated embodiment, aspiration system 705 represents an embodiment of the sample removing system. Aspiration system 705 can be configured to urge at least a portion of the cartridge into the sealed container and remove a fluid sample into the cartridge. Aspiration system 705 can include any of a variety of configurations of valves, tubes, probes, pumps, aspirators, or the like effective for moving fluids and for coupling to a cartridge. Aspiration system 705 may also be configured to invert the cartridge, the sealed container, or both.

In this illustrated embodiment, optional fluid processing system 707 represents an embodiment of a portion of the cartridge handling system. Fluid processing system 707 can be configured to heat, shine light on, irradiate, add reagent to, remove reagent from, or otherwise process the fluid sample obtained by aspiration system 705. Fluid processing system 707 can include any of a variety of configurations of light sources, heaters, reagent dispensers, valves, tubes, probes, pumps, actuators, or the like effective for treating a fluid sample in a vessel.

In this illustrated embodiment, fluid dispensing system 709 represents an embodiment of another portion of the cartridge handling system. Fluid dispensing system 709 can be configured to place a fluid sample obtained in a cartridge into a predetermined container, such as a particular well of a microtiter plate. Fluid dispensing system 709 can be configured to place each of a plurality of fluid samples into each of a corresponding plurality of wells. Fluid dispensing system 709 can include any of a variety of configurations of valves, tubes, probes, pumps, actuators, or the like effective for dispensing a fluid sample into a container.

In this illustrated embodiment, aliquot conveyor 711 represents an embodiment of a portion of rack transport system. Aliquot conveyor 711 can be configured to transport a container, such as a microtiter plate from fluid dispensing system 709 to the surroundings. Aliquot conveyor 711 can be or can include any of a variety of conveyors suitable for carrying a container such as a microtiter plate.

The automation system of the invention can be used to automate functions of the present system or procedures employed in the present method, several of which are described above. Components of the automation system can also invert a rack of samples or cartridges.

Referring again to FIG. 13, an automated embodiment of the present system can engage container support 400 and/or cartridge array 300 and can operate latch 403 (shown in FIG. 15). Engaging the container support 400 and operating the latch 403 can secure this assembly in the system and can couple the two components of the assembly to one another. As shown in FIG. 13, an automated embodiment of the present system can move a tube within container support 400 from a position disengaged from cartridge array 300 (right hand two tubes) to a position coupled to cartridge array 300 (left and tube). The system can include a push rod, an array of rods, or the like configured to move the sample tubes relative to the container support 400. The rods or other configuration for moving the tubes can enter container support 400 through apertures 510. The rods move relative to the container support 400. Therefore, the rods may be stationary or may move. The container support 400 may be stationary or may move.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, adapted and configured, constructed and arranged, adapted, constructed, manufactured and arranged, and the like.

Directions used herein are only to describe relations in a relative manner. For example, something described as on the top of an object may also be considered to be on the bottom of the object depending on the orientation of the object. Further, descriptions herein of the movement of objects are relative. For example, when an object is described to move it may actually be stationary and other objects may move.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. An apparatus comprising:
   a support body defining a number of aligned tube holders, each tube holder sized to receive a sealed container; and
   a cartridge detachably secured to the support body, the cartridge including an array of fluid receptacles, each fluid receptacle including:
   i) a reservoir defined by housing structure;
   ii) a piercing conduit that provides fluid communication between one corresponding sealed container and the reservoir;
   iii) a venting system that vents the corresponding sealed container to exterior surroundings; and
   iv) a filling system that draws a sample from the corresponding sealed container into the reservoir;
   v) wherein the piercing conduit provides fluid communication between the corresponding sealed container and the reservoir when the venting system vents the sealed container to the exterior surroundings, and wherein the piercing conduit provides fluid communication between the corresponding sealed container and the reservoir when the filling system draws the sample from the sealed container into the reservoir.

2. The apparatus of claim 1, wherein the number of fluid receptacles in the array of fluid receptacles corresponds to the number of aligned tube holders.

3. The apparatus of claim 1, wherein the housing structures of each fluid receptacle are integral with one another, the integral housing structures at least partly defining the cartridge.

4. The apparatus of claim 1, wherein the cartridge defines the housing structures of each of the fluid receptacles.

5. The apparatus of claim 1, wherein the venting system is positionable in an open configuration and a closed configuration, the venting system providing the fluid communication between the sealed container and the exterior surroundings when in the open configuration, the venting system preventing fluid communication between the sealed container and the exterior surroundings when in the closed configuration.

6. The apparatus of claim 1, wherein the filling system includes a first piston that sealingly engages the housing structure, and a second piston that sealingly engages the first piston, the second piston being configured to move relative to the first piston.

7. The apparatus of claim 6, wherein the first piston and the housing structure defining a sample chamber, and the second piston and the first piston define a venting chamber.

8. The apparatus of claim 6, wherein the second piston is positionable in an open position relative to the first piston at which the corresponding sealed container vents to the exterior surroundings, and a closed position relative to the first piston at which the corresponding sealed container is prevented from venting to the exterior surroundings.

9. The apparatus of claim 8, wherein the sample is drawn from the corresponding sealed container by the filling system only when the second piston is positioned in the closed position.

10. The apparatus of claim 9, wherein the sample is drawn from the sealed container by moving the first piston.

11. The apparatus of claim 10, wherein the second piston moves in unison with the first piston when the sample is drawn from the sealed container.

12. The apparatus of claim 1, further including a filter located within the fluid receptacle that filters flow between the corresponding sealed container and the exterior surroundings.

13. The apparatus of claim 12, wherein the filter retains liquid and solid, and permits gasses to vent to the exterior surroundings.

14. The apparatus of claim 1, wherein each fluid receptacle is individually detachable from the cartridge.

* * * * *